(12) United States Patent
Nakajima et al.

(10) Patent No.: US 9,064,922 B2
(45) Date of Patent: Jun. 23, 2015

(54) SUBSTRATE INSPECTION APPARATUS AND SUBSTRATE INSPECTION METHOD

(75) Inventors: Taigo Nakajima, Kyoto (JP); Kunio Ueta, Kyoto (JP); Kazutaka Taniguchi, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 257 days.

(21) Appl. No.: 13/808,939

(22) PCT Filed: Jan. 6, 2012

(86) PCT No.: PCT/JP2012/000055
§ 371 (c)(1),
(2), (4) Date: Jan. 8, 2013

(87) PCT Pub. No.: WO2012/132166
PCT Pub. Date: Oct. 4, 2012

(65) Prior Publication Data
US 2013/0114074 A1    May 9, 2013

(30) Foreign Application Priority Data

Mar. 30, 2011 (JP) ................... 2011-074423
Sep. 29, 2011 (JP) ................... 2011-215166

(51) Int. Cl.
G06K 9/00      (2006.01)
H01L 21/68     (2006.01)
H01L 21/67     (2006.01)
G01N 21/84     (2006.01)
H01L 21/66     (2006.01)

(52) U.S. Cl.
CPC ........ *H01L 21/681* (2013.01); *H01L 21/67288* (2013.01); *H01L 22/12* (2013.01); *G01N 21/8422* (2013.01); *G01N 2021/8427* (2013.01); *H01L 2924/0002* (2013.01)

(58) Field of Classification Search
None
See application file for complete search history.

(56) References Cited

U.S. PATENT DOCUMENTS

| 7,046,353 | B2 * | 5/2006 | Isozaki et al. ............. 356/237.2 |
| 7,616,804 | B2 | 11/2009 | Pai et al. ...................... 382/145 |
| 7,865,010 | B2 | 1/2011 | Pai et al. ...................... 382/145 |
| 8,111,372 | B2 * | 2/2012 | Kyouda et al. ................. 355/27 |

(Continued)

FOREIGN PATENT DOCUMENTS

| JP | 2006-352113 | 12/2006 |
| JP | 2009-010349 | 1/2009 |

(Continued)

OTHER PUBLICATIONS

International Search Report mailed Mar. 6, 2012 in corresponding PCT International Application No. PCT/JP2012/000055.

(Continued)

*Primary Examiner* — Daniel Mariam
(74) *Attorney, Agent, or Firm* — Ostrolenk Faber LLP

(57) ABSTRACT

A substrate inspection apparatus for detecting a condition of an EBR line at a substrate edge, comprising a turntable for rotating a substrate having a film coated thereon, a light irradiator and a photoelectric converter that receives specularly reflected light from the substrate and outputs a captured image signal. A two-dimensional image is generated by adding detection values of electrical signals corresponding to one radial scan from a center of the substrate for one turn of a rotator, and a changing point is judged using a judgment band set along one direction of the two-dimensional image.

14 Claims, 11 Drawing Sheets

(56) References Cited

U.S. PATENT DOCUMENTS

| | | | |
|---|---|---|---|
| 8,175,372 B2 | 5/2012 | Pai et al. | 382/145 |
| 2006/0286811 A1 | 12/2006 | Heiden et al. | 438/759 |
| 2008/0292780 A1 | 11/2008 | Vangheluwè et al. | 427/8 |

FOREIGN PATENT DOCUMENTS

| | | |
|---|---|---|
| JP | 2009-544157 | 12/2009 |
| JP | 2010-276582 | 12/2010 |
| JP | 2011-009626 | 1/2011 |
| KR | 10-2006-0107196 | 10/2006 |
| KR | 10-2010-0053038 | 5/2010 |
| WO | WO 2010/028353 | 3/2010 |

OTHER PUBLICATIONS

Korean Notice of Allowance issued Aug. 13, 2014 for corresponding Korean Patent Application No. 10-2012-7027708 (2 pages).

Taiwan Office Action issued May 12, 2014 for corresponding Taiwanese Patent Application No. 101100215 (6 pages).

* cited by examiner

F I G. 1
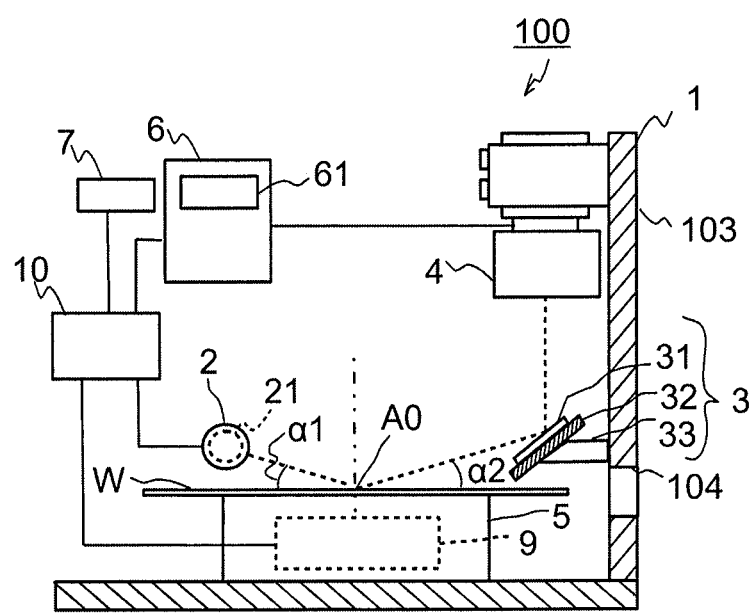

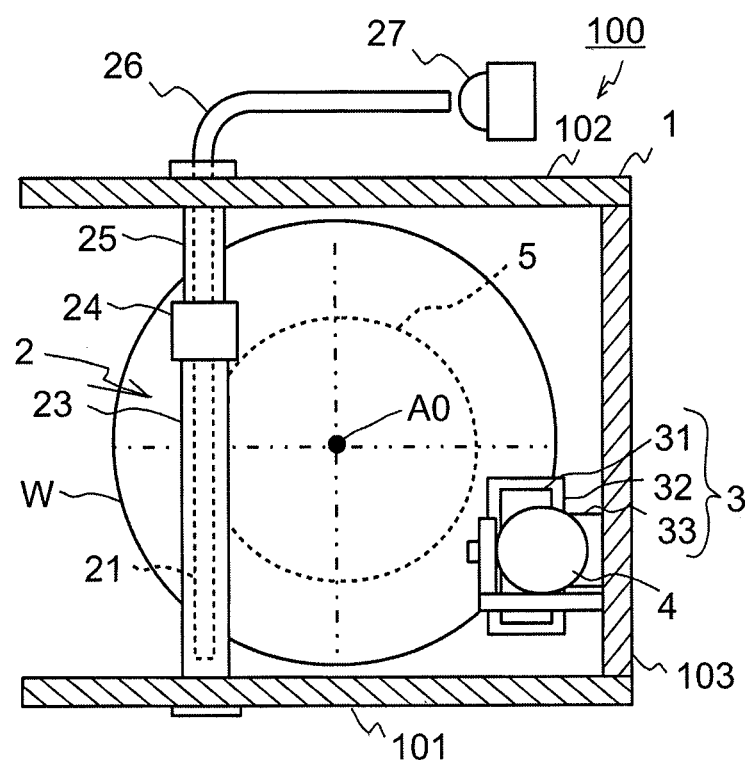
F I G. 2

FIG. 12A: RELATIONSHIP BETWEEN EBR LINE AND JUDGMENT BAND (PERMISSIBLE WIDTH)

| | NUMBER OF EBR LINES | | | | | | |
|---|---|---|---|---|---|---|---|
| | FIRST | | SECOND | | ... | mTH | |
| | INNER DIAMETER xna | OUTER DIAMETER xnb | INNER DIAMETER xna | OUTER DIAMETER xnb | ... | INNER DIAMETER xna | OUTER DIAMETER xnb |
| PROCESSING 1 | x11a | x11b | x12a | x12b | ... | x1ma | x1mb |
| PROCESSING 2 | x21a | x21b | x22a | x22b | ... | x2ma | x2mb |
| ... | ... | ... | ... | ... | ... | ... | ... |
| PROCESSING n | xn1a | xn1b | xn2a | xn2b | ... | xnma | xnmb |

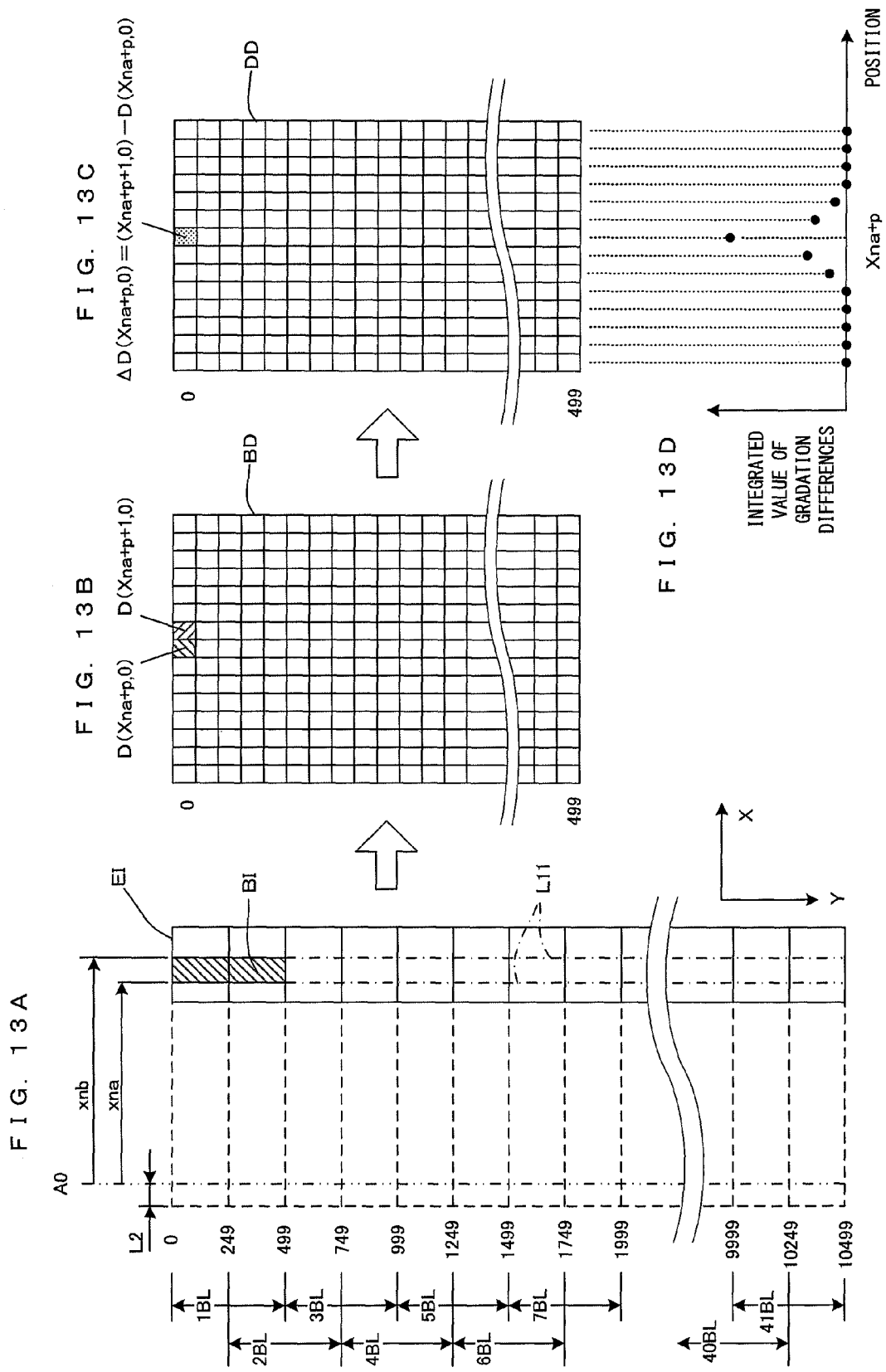

SUBSTRATE INSPECTION APPARATUS AND SUBSTRATE INSPECTION METHOD

CROSS-REFERENCE TO RELATED APPLICATIONS

The present application is a 35 U.S.C. §§371 national phase conversion of PCT/JP2012/000055, filed Jan. 6, 2012, which claims priority of Japanese Patent Application No. 2011-074423, filed Mar. 30, 2011, and Japanese Patent Application No. 2011-215166, filed Sep. 29, 2011, the contents of which are incorporated herein by reference. The PCT International Application was published in the Japanese language.

TECHNICAL FIELD

This invention relates to substrate inspection apparatus and inspection method and particularly to a field of technology for inspecting a coating film on a substrate based on a captured image.

BACKGROUND ART

It is known to a person skilled in the art that a transparent film, e.g. a photoresist film formed by applying a resist, e.g. in a manufacturing process of semiconductor devices to form a multitude of semiconductor devices on a semiconductor wafer cut out from a single crystal lot, is selectively etched to form first conductive semiconductor layers, electrodes and leads of desired shapes. Mask alignment is performed in every one of these steps. Since a state of a resist surface, e.g. a change in film thickness, foreign matters, scratches cause semiconductor defects, they are requested to be found in early steps.

The photoresist spreads to form a thin coating on the surface by rotating the wafer about a center axis at a high speed. Due to an edge surface effect, the photoresist deposits on the edge of the wafer. Thus, it is known to be necessary to remove the photoresist on the edge (EBR process).

Accordingly, there has been provided an inspection method for inspecting the perfection of the photoresist removal and a predetermined position of a boundary line between an area including the photoresist and an area not including the photoresist, i.e. an edge bead removal line (EBR line) (JP2006-352113A). In this JP2006-352113A, an image area on a surface of a wafer is irradiated using light in a wavelength range of 360 nm to 500 nm and a fluorescence image in the image area is reflected from fluorescent light emitted due to irradiation by excitation light to identify a fluorescent EBR line.

However, since a dark-field image is obtained in JP2006-352113A, resolution (resolving power) itself is not improved. A feature of a dark-field illumination method is that the use is basically difficult for thick specimens. Further, it is necessary to use a photoresist added with a fluorescent dye and a fluorescent EBR solution. In inspecting the coating film of the photoresist, there is a disadvantage that an arbitrary inspection target cannot be dealt with if the coating film itself requires ingenuity.

Further, a device with a CCD camera extending over an entire substrate surface is provided as a substrate inspection apparatus (JP2009-10349A). By plotting data on polar coordinates, a substrate to be rejected is selected which has a risk of increasing contamination due to the overlap of lines corresponding to a BARC layer, a top coat layer and a resist layer on an edge part of the substrate.

However, it is only mentioned in JP2009-10349 to select a substrate having an overlap on an edge part in each layer as a substrate to be rejected. Thus, although it is mentioned to fit a curve to data for automatic analysis in addition to visual judgment in testing a substrate, it is not clear how automatic analysis is performed other than based on the overlap on the edge part. Therefore, there has been room for improvement as to whether or not promotion of streamlining is possible.

Further, an edge feature measurement system has been provided which detects a relative distance from an edge part of a wafer to that of a resist layer via an imaging system (JP2009-544157A). In this system, pixel arrays having a plurality of first dimension X and second dimension Y are acquired around a wafer edge area and an edge map is generated from the respective pixel arrays. The intersection of a layer is evaluated and measured or another characteristic is determined from an image covering around the wafer.

However, these systems are complicated since an image is generated by mapping. Specifically, an overall evaluation cannot be made unless the edge map is completed. On the other hand, overlapping areas are easily formed on boundaries between the pixel arrays if the pixel arrays as a basis are large, whereas it is necessary and complicated to verify optimization for an evaluation target area of the wafer edge part if the pixel arrays are small.

SUMMARY OF THE INVENTION

Technical Problem

As described above, in the above conventional technology, an edge part image can be formed and evaluated by being divided into small areas, but the entire image is generated for the evaluation of the entire edge part and the process takes time. Particularly, the evaluation of the EBR line means the occurrence of misalignment between the wafer center and the resist layer due to many factors in various workings and processings in several manufacturing processes caused thereby. Thus, it is preferable to evaluate in many processes and more efficient inspection is desired since evaluation is made between processings.

Further, as with the conventional technology, misalignment which is a deviation from the desired alignment, e.g. a relative position from the edge part of the wafer to that of the resist layer is also a necessary evaluation item in the evaluation of the wafer edge part besides the overlap of the edge part of each layer, but inspection has not been efficiently made.

Solution to Problem

In order to solve the above problems, a substrate inspection apparatus according to claim 1 of the present invention comprises: a rotator that holds and rotates a substrate having a coating film formed on a surface; a light irradiator that irradiates light to the surface of the substrate; a photoelectric converter that receives specularly reflected light from the surface of the substrate and captures an image of a scanning line having at least a length of the radius of the substrate in a main scanning direction parallel to a radial direction of the substrate from a center of rotation of the substrate; and an image processor that generates a two-dimensional image by arranging images captured by the photoelectric converter during one turn of the substrate in a sub scanning direction perpendicular to the main scanning direction and judges whether an edge line of the coating film is good or bad using a judgment band set in parallel to the sub scanning direction for the two-dimensional image.

Further, a substrate inspection method according to claim 8 of the present invention comprises: a capturing step of capturing an image of a scanning line having at least a length of the radius of a substrate having a coating film formed on the surface in a main scanning direction parallel to a radial direction of the substrate from a center of rotation of the substrate by irradiating light to the surface of the substrate while rotating the substrate, and receiving specularly reflected light from the surface of the substrate; an image generating step of generating a two-dimensional image by arranging images obtained by repeating the capturing step during one turn of the substrate in a sub scanning direction perpendicular to the main scanning direction; and a judging step of judging whether an edge line of the coating film is good or bad using a judgment band set in parallel to the sub scanning direction for the two-dimensional image.

Further, in the substrate inspection apparatus according to claim 1, the image processor includes: an edge detector that divides an image included in the judgment band out of the two-dimensional image into a plurality of block images in the sub scanning direction and detects whether or not each block image includes the edge of the coating film; and a good and bad judgment unit that judges whether the edge line of the coating film is good or bad based on the number of the edge-detected block images by the edge detector.

Further, in the substrate inspection apparatus according to claim 2, the edge detector divides the image such that the block images adjacent to each other partly overlap in the sub scanning direction.

Further, in the substrate inspection apparatus according to claim 1, the image processor specifies the edge line included in the two-dimensional image, calculates a changing point based on the presence or absence of the edge line within the width of the judgment band and judges an edge defect in the absence of the edge line.

Further, in the substrate inspection apparatus according to any one of claims 1 to 4, the scanning line captured by the photoelectric converter has a length which is the sum of the radius of the substrate and a first length in the main scanning direction from the center of rotation.

Further, in the substrate inspection apparatus according to any one of claims 1 to 5, the scanning line captured by the photoelectric converter extends a second length in a direction opposite to the main scanning direction from the center of rotation.

Further, in the substrate inspection apparatus according to any one of claims 1 to 6, a plurality of coating films are laminated on the surface of the substrate; judgment bands are set in correspondence with the respective coating films; and the image processor judges whether an edge line of each coating film is good or bad using the judgment band corresponding to each coating film.

Advantageous Effects of Invention

According to the substrate inspection apparatus according to the first aspect of the invention and the substrate inspection method according to the eighth aspect thereof, an operation of obtaining a line image by capturing an image of a scanning line having at least a length of the radius of the substrate in the main scanning direction parallel to the radial direction of the substrate from the center of rotation of the substrate is performed during one turn of the substrate to obtain a plurality of line images. Then, a two-dimensional image is generated by arranging these line images in the sub scanning direction perpendicular to the main scanning direction, and whether an edge line of the coating film is good or bad is judged using a judgment band set in parallel to the sub scanning direction for this two-dimensional image. This produces effects that the evaluation of the coating film can be easily judged from the captured image of the substrate and inspection/detection with good processing efficiency can be made.

Further, according to the substrate inspection apparatus according to the second aspect of the invention, the image included in the judgment band out of the two-dimensional image is divided into a plurality of block images in the sub scanning direction, whether or not each block image includes the edge of the coating film is detected and whether the edge line of the coating film is good or bad is judged based on the number of the edge-detected block images. Thus, the edge of the coating film in each part of the substrate can be detected and an edge defect can be judged by a simple detection process.

Further, according to the substrate inspection apparatus according to the third aspect of the invention, since the image is divided such that the block images adjacent to each other partly overlap in the sub scanning direction, the edge of the coating film can be detected with high accuracy and an edge defect can be more precisely judged.

Further, according to the substrate inspection apparatus according to the fourth aspect of the invention, the image processor specifies the edge line in the two-dimensional image and calculates the changing point based on the presence or absence of the edge line within the width of the judgment band. Then, an edge defect is judged in the absence of the edge line. Thus, evaluation by the changing point can be made and an edge defect can be judged by a simple comparison.

Further, according to the substrate inspection apparatus according to the fifth aspect of the invention, the scanning line has the length, which is the sum of the radius of the substrate and the first length, in the main scanning direction from the center of rotation, i.e. is extended by the first length, and an extended part functions as a margin when the substrate is misaligned. As a result, an edge defect can be judged even if the substrate is misaligned.

Further, according to the substrate inspection apparatus according to the sixth aspect of the invention, the scanning line captured by the photoelectric converter extends the second length in the direction opposite to the main scanning direction from the center of rotation and is extended by the second length. As in the case of extending the scanning line by the first length as described above, an extended part of the scanning line functions as a margin when the substrate is misaligned. As a result, an edge defect can be judged even if the substrate is misaligned.

Furthermore, according to the substrate inspection apparatus according to the seventh aspect of the invention, the judgment bands corresponding to the respective coating films laminated on the surface of the substrate are set, and whether the edge line of each coating film is good or bad is judged using the judgment band corresponding to each coating film. Thus, even if a plurality of coating films are laminated on the surface of the substrate, an edge defect of each coating film can be precisely judged.

BRIEF DESCRIPTION OF DRAWINGS

FIG. 1 is a front view showing a first embodiment of a coating film formation nonuniformity inspection apparatus of the invention.

FIG. 2 is a plan view of the coating film formation nonuniformity inspection apparatus shown in FIG. 1.

FIG. 13 is a diagram schematically showing the edge detection operation in the second embodiment.

DESCRIPTION OF EMBODIMENTS

Figure 3:
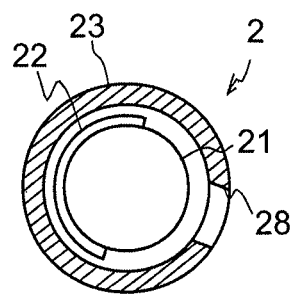
FIG. 3 is a sectional view of an essential part of a light irradiator.

Hereinafter, a first embodiment of the invention is described with reference to FIGS. 1 to 5.

First, with reference to FIGS. 1 and 2, a basic configuration and functions of the first embodiment of the invention are described. FIG. 1 is a front view of an inspection apparatus and FIG. 2 is a plan view of the inspection apparatus.

Note that a coating target of the invention is a circular semiconductor wafer and a film with a transparent surface is a resist film made of a photosensitive material and formed on a surface of the semiconductor wafer in each semiconductor device manufacturing step. An embodiment applied to an inspection apparatus for an edge resist film on the semiconductor wafer surface, for example, to measure a change in an EBR line on a photoresist surface after coating is described with reference to the drawings. Note that, without being limited to the resist film, a misalignment of an edge part of an anti-reflection material applied beneath the resist film and made of, e.g. polyimide resin or a top coat adapted to protect the resist film and made of, e.g. alkali soluble polymer and alcohol solvent may be measured.

As shown in FIG. 1, in a substrate inspection apparatus 100, a turntable 5, a light irradiator 2 including a light source 21, an optical system 3 and a photoelectric converter 4 are housed in a detection unit 1. W denotes a substrate such as a semiconductor wafer which is a coating target (hereinafter, referred to as substrate W), and 5 denotes the turntable as a rotator. The substrate W is held and rotated to inspect the entire surface by being sucked to a circular table upper surface by a sucker formed by an unillustrated suction hole by vacuum. The substrate W is rotated by more than one turn by the turntable 5 to inspect the entire surface.

The light irradiator 2 is arranged vertically above the substrate W held on the turntable 5. The light irradiator 2 is such that the light source 21 formed of a light guide made of a quartz rod is inserted in a cylindrical supporting portion 23 made of aluminum, one end of the cylindrical supporting portion 23 is fixed to a side wall 101 of the detection unit 1 and the other end is fixed to another side wall 102 via a connecting portion 24 and a connecting tube 25.

The light irradiator 2 is described in more detail. FIG. 3 is a sectional view of an essential part of the light irradiator 2.

With reference to FIG. 3, a reflector 22 is mounted on a part of the peripheral surface of the light source 21. Most of light reflected by the reflector 22 is emitted from a side opposite to the reflector 22. A slit 28 is formed in the cylindrical supporting portion 23 at this side opposite to the reflector 22. Thus, the light emitted from the light source 21 is blocked by the cylindrical supporting portion 23 and irradiated toward the substrate W through the slit 28.

Referring back to FIG. 2, the light source 21 is connected to one end of an optical fiber 26 by the connecting portion 24, and this optical fiber 26 extends through the interior of the connecting tube 25 to the outside of the detection unit 1 from the side wall 102. The other end of the optical fiber 26 is opposed to an LED 27 arranged outside the detection unit 1. By doing so, when the LED 27 is turned on, the light thereof is introduced to the light source 21 via the optical fiber 26. The light introduced to the light source 21 is radiated from the periphery of the quartz rod and irradiated through the slit 28.

Referring back to FIG. 1, a line sensor camera as the photoelectric converter 4 is, for example, arranged vertically above the substrate W. A known line sensor camera composed of a line sensor element such as a CCD or a MOS, an amplifier, a drive circuit, an A/D converter, a memory, an input/output circuit, an imaging lens (taking lens), a housing and the like can be used as such a line sensor camera.

Light incident on this photoelectric converter 4 is specularly reflected light from the surface of the resist film by light irradiated from the light irradiator 2 which light forms a line in a radial direction including a center of rotation A0 of the substrate W. Specifically, a part of the light from the light source 21 is incident on the surface of the resist film. An angle of incidence a1 at this time is preferably 20° to 40°, more preferably 30° to the resist film surface. The optical system 3 is so arranged that a specular reflection light path of the specularly reflected light substantially corresponding to the radius of the substrate W by this incidence is incident on a lens of the photoelectric converter 4. Note that substrate size is desirably also taken into consideration for the angle of incidence a1. The angle of incidence a1 is desirably set at the above angle when the substrate W is a presently mainstream 300-mm semiconductor wafer, but is desirably set at about 45° for a larger substrate W, e.g. a next-generation 450-mm semiconductor wafer.

The optical system 3 is composed of a rectangular and planar mirror 31 and a holding plate 32 for holding the mirror 31. The holding plate 32 is mounted on a side wall 103 of the detection unit 1 and fixed to introduce the specularly reflected light having an angle of reflection α2 from the substrate W to the photoelectric converter 4 located right above after the angle of the mirror 31 is adjusted.

Figure 4:
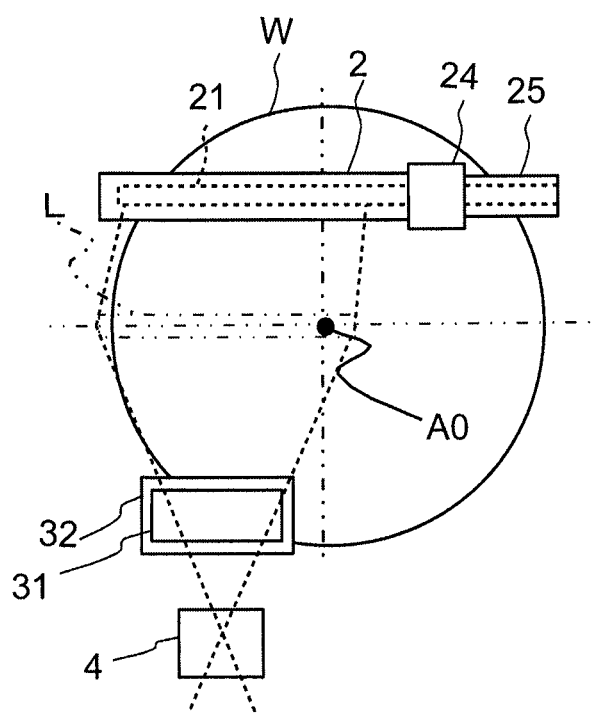
FIG. 4 is a schematic diagram showing a light path in the coating film formation nonuniformity inspection apparatus.

FIG. 4 is a schematic diagram showing a light path from the light irradiator 2 to the photoelectric converter 4 in the substrate inspection apparatus 100. Although the photoelectric converter 4 is displaced so that the specular reflection light path can be seen in FIG. 4, the photoelectric converter 4 is arranged substantially vertically above the optical system 3 as shown in FIG. 2. As shown by dotted line in FIG. 4, the specularly reflected light from the substrate W is received by the photoelectric converter 4 via a light receiving lens inside and converted into an electrical signal.

This electrical signal is processed in an image processing apparatus 6 which is an image processor as a signal processor and a surface state of the substrate W is detected in a controller 10. To introduce the specularly reflected light having the angle of reflection α2 from the substrate W to the photoelectric converter 4 located right above, the angle of the mirror 31 and a distance thereof to the photoelectric converter 4 are so adjusted and set that a reduced image of an imaging area L which is a scanning line on the substrate W is imaged on a light receiver of the photoelectric converter 4.

Referring back to FIG. 1, the turntable 5 is provided on a drive mechanism platform and the substrate W is sucked as if it were correctly adhering to the table surface when being placed on the turntable 5. A motor 9 is arranged in the drive mechanism platform and a speed change gear for converting the rotation from the motor 9 into a predetermined speed is provided. The motor 9 is controlled by the controller 10 to be described later.

The substrate W during a semiconductor manufacturing process having the resist film provided on the surface is placed on the turntable 5 with the resist film faced upward. A carrier used here forms a system line for sucking the underside where the resist film is not provided such as by driving a robot for each inspection in the semiconductor manufacturing process and transferring the substrate W through an opening 104 of the side wall 103, and sucking the substrate W by a conveyor robot and transferring it to the next step after the inspection is finished.

Further, unillustrated work transfer robot as a loader and an unloader for substrates W and cassette are provided. The work transfer robot picks the substrate W out of the cassette, sets it on the turntable 5 and accommodates that substrate W on the turntable 5 to the cassette after the inspection is finished. In this case, the substrates W may be sorted out based on an inspection result by preparing cassettes for OK and NG 7 denotes a power supply device for supplying power to each component in the detection unit 1, and 10 denotes the controller for processing electrical signals together with the image processing apparatus 6 and making a good or bad judgment. An output signal of the photoelectric converter 4 is amplified and input to the image processing apparatus 6, and processed in this image processing apparatus 6, whereby change information of the edge part of the substrate W is subjected to electrical waveform shaping and input to the controller 10. This image processing apparatus 6 has a built-in judging function, an output signal of the image processing apparatus 6 is arithmetically processed by a computer or the like, and the presence or absence of a change in the coating film formation is judged and a good or bad judgment is made by an evaluator 61. Note that this judgment result is returned to the image processing apparatus 6 and displayed on an unillustrated display such as a television monitor. When it is desired to move the substrate W according to an inspection status in the image processing apparatus 6, the controller 10 drives the turntable 5 via the motor 9.

Figure 5:
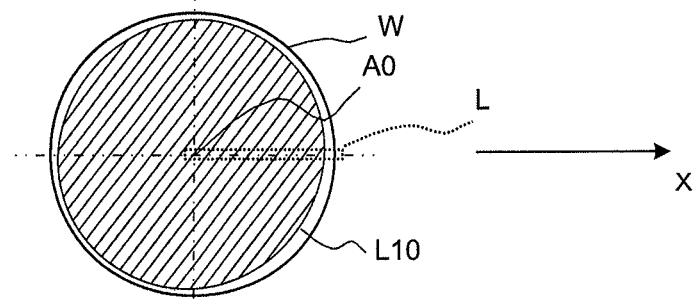
FIG. 5 is a plan view showing a surface state of a substrate W after an EBR process of a resist film.
Figure 6:
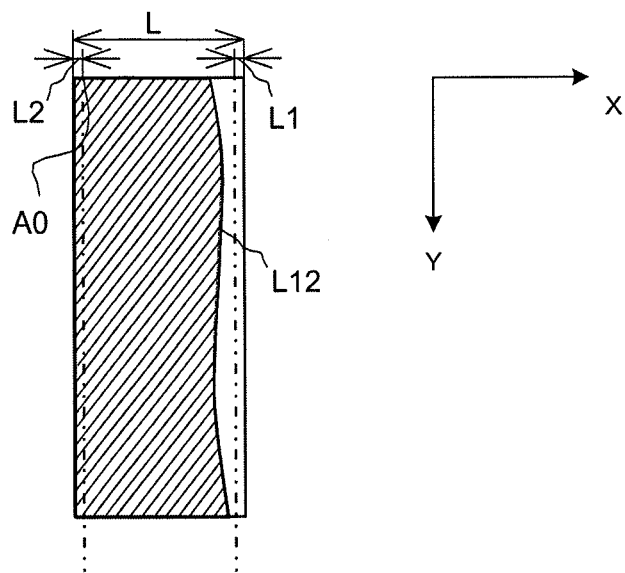
FIG. 6 is a diagram showing digital signal of an image of the substrate W.

Next, a specific example of image processing by the image processing apparatus 6 is described with reference to FIGS. 5 and 6. FIG. 5 is a plan view showing a surface state of the substrate W after the EBR process of the resist film, and FIG. 6 shows a digital signal of an image of the substrate W. A hatched inner part and an outer part at inner and outer sides of a boundary shown by a curve L10 in the substrate W in FIG. 5 are parts which differ in the presence or absence of a resist layer. Specifically, the curve L10 is an EBR line and the part at the outer side of the curve L10 shows a state where the resist layer is removed and the surface of the substrate W is exposed.

The imaging area L shown by dotted line in FIG. 5 is an exposure area by the light source 21 and serves as an imaging area by the photoelectric converter 4. Specularly reflected light in the imaging area L by the photoelectric converter 4 is converted into a digital signal by a photoelectric converter (A/D converter) and output.

The imaging area L is set such that the length of a scanning line is longer than the radius of the substrate W by 2 mm as an area L1 outside the substrate W and 2 mm as an area L2 at the center of rotation A0 side of the substrate W. Such setting forms margins for the misalignment of the substrate W. A line width of the imaging area L is set such that one line is captured every 360 pec at a pixel resolution of 30 μm. Thus, about 10000 lines are captured and output while the substrate W is turned 360°, i.e. makes one turn for 3.6 sec. As just described, in the first embodiment, the scanning line is a line extending in a main scanning direction X parallel to a radial direction of the substrate W and has a length, which is the sum of the radius of the substrate W and the length of the area L1, in the main scanning direction X (toward the right side of FIG. 6) from the center of rotation A0 of the substrate W and has a length of the area L2 in a direction (toward the left side of FIG. 6) opposite to the main scanning direction X from the center of rotation A0.

The digital signal of the image of the substrate W thus obtained is shown in FIG. 6. FIG. 6 shows a two-dimensional shape in which the lines captured while the substrate W is turned 360°, i.e. makes one turn are arranged. This digital signal is stored as a two-dimensional image in the memory. In the image processing apparatus 6, a judgment to be described later is made in the evaluator 61 based on this data of FIG. 6. That is, in the first embodiment, the two-dimensional image is generated by arranging the images of the scanning lines captured every 360 μsec as described above in a sub scanning direction Y perpendicular to the main scanning direction X.

Figure 7:
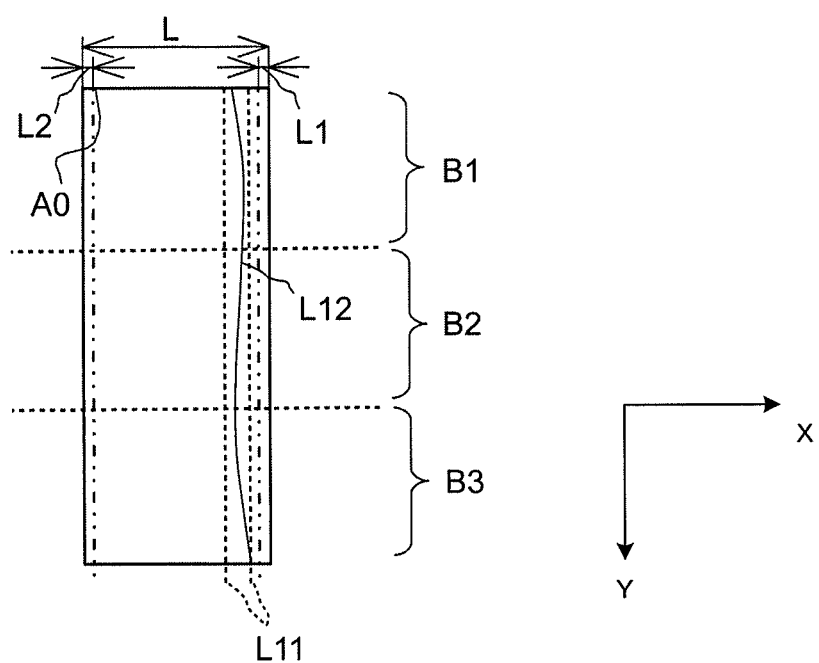
FIG. 7 is a diagram showing an EBR line and a judgment band.

FIG. 7 is a diagram showing a judgment band for the two-dimensional image of the substrate W obtained by the photoelectric converter 4. If the images of the respective pixels in the imaging area L captured during one turn of the substrate W are arranged over the entire periphery at positions equidistant from the center of rotation A0, the two-dimensional image as shown in FIG. 6 is obtained. Here, an electrical signal corresponding to a captured light amount detected in the imaging area L varies due to the interference of a thin film. The image processing apparatus 6 digitizes this captured light amount by converting it into an image electrical signal corresponding to the captured light amount in 256 gradations of 8 bits for each pixel. Here, a relationship is so set that the larger the light amount, the higher the gradation.

Then, an evaluation process as shown in FIG. 7 is performed. A changing point where a luminance change is large is extracted from the image electrical signal by digitizing the image obtained during one turn of the substrate W as shown in FIG. 6 by the image processing apparatus 6. Specifically, luminance differs on the edge part of the substrate W depending on the presence or absence of the resist film. In other words, since a luminance change largely differs at the position of the EBR line, an edge line L12 is generated by extracting this boundary. By extracting the EBR line over the entire periphery of the substrate W, the edge line L12 is obtained as shown in FIG. 7.

The following process is performed in the image processing apparatus 6 to enhance this edge line L12. For example, the two-dimensional image is divided into three blocks B1, B2 and B3 as shown by two dotted lines. Subsequently, digital values of the image electrical signals of the scanning lines are integrated per pixel for each block. Then, a difference between a high-luminance region and a low-luminance region is emphasized, but data near an intermediate value is more or less seen due to luminance noise in some cases. Specifically, luminance is high at the edge side of the substrate W where there is no resist film, but if there is a residue of the resist film, a low-luminance region is produced. In each of a region where the resist film is present and a region where the resist film is absent, the integrated values per pixel are approximate integrated values as a whole. However, if the low-luminance region is present in the high-luminance region, it is thought to be a residue of the resist film. Thus, the integrated value of such a region is deleted and set to be equal to the integrated value of the high-luminance region.

A collection of the integrated values, some of which are deleted and changed, are expanded again into a two-dimensional image block by block. By doing so, digital values having noise removed are two-dimensionally expanded and differences in the digital values per pixel between the region where the resist film is present and the region where the resist film is absent become clear at opposite sides of the edge line L12 as a boundary in the two-dimensional image shown in FIG. 7. As a result, the edge line 12 is enhanced.

The judgment band L11 is input and set in the evaluator 61 from an unillustrated input device by an operator in advance. Here, a position where the EBR line is supposed to be present from the edge part of the substrate W toward the center of rotation A0 side of the substrate W is input as a distance. Then, a permissible amount of deviation of the EBR line from this position where the EBR line is supposed to be present is set as a distance. A line set to have an equal width with this position where the EBR line is supposed to be present as a center is set as the judgment band L11 in the evaluator 61.

The evaluator 61 superimposes the judgment band L11 on the two-dimensional image when the EBR line is extracted. As a result of this superimposition, a region where the EBR line is not located within the judgment band L11 on the two-dimensional image is judged as a changing point. Specifically, a point where the edge line L12 is not within the width of the judgment band L11 is detected as a changing point for each scanning line. The evaluator 61 detects and outputs this changing point, whereby the image processing apparatus 6 makes a good or bad judgment and the like. The result of the good or bad judgment by the image processing apparatus 6 is displayed on the unillustrated display via the controller 10 to indicate that the EBR line is not at a predetermined position. Thus, the image processing apparatus 6 and a part of the controller 10 correspond to an image processor of the invention.

Figure 8:
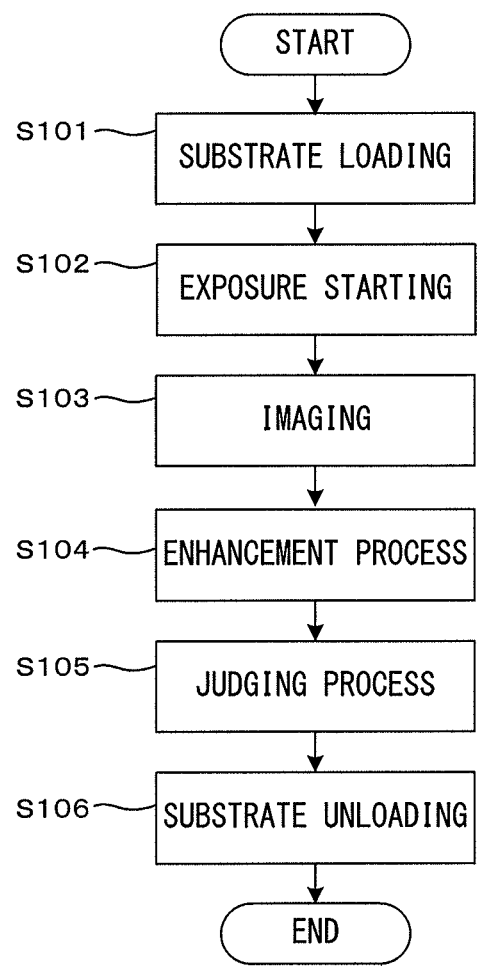
FIG. 8 is a flow chart showing a processing operation.

Next, an inspection operation by this substrate inspection apparatus 100 is described. FIG. 8 is a flow chart showing a processing operation. When the substrate W is placed on the turntable 5 (Step S101), the exposure of the surface of the substrate W to light is started by the light irradiator 2 (Step S102). If the coating film is present on the substrate W, light from the light source 21 is caused to scatter or interfere by this coating film and a part of specularly reflected light thereof is imaged without being incident on the photoelectric converter 4. Unless the coating film is present, the illuminating light is totally reflected on the substrate W and specularly reflected light is incident on the photoelectric converter 4. Note that it is assumed in this embodiment that light is specularly reflected by a normal coating film, although it may be opposite depending on the film.

At this time, a thin film of the resist is formed on the surface of the substrate W and an image of the specularly reflected light looks to have a different color depending on a difference in the thickness of the resist or whether the coating film is present or absent. Note that since the resist material is a photosensitive material and photosensitized by ultraviolet rays, light from the LED 27 has ultraviolet rays cut by a filter or the like. Particularly, after the EBR process, the color of the region where the surface of the substrate W is exposed and that of the region where the resist film is present largely differ.

Accordingly, the amount of the specularly reflected light can be detected by imaging by the photoelectric converter 4. This means that a change in the thickness of the resist layer on the substrate W can be imaged by the photoelectric converter 4. The position of the EBR line is also imaged.

Subsequently, the turntable 5 is rotated while the substrate W is exposed to light and the imaging area L is continuously captured during one turn of the substrate W (Step S103). Then, the captured image per pixel forming one scanning line obtained during one turn of the substrate W is obtained as shown in FIG. 6. Note that a corrected image electrical signal may be obtained by subtracting an irradiation electrical signal of the light source 3 measured in the imaging area L from the image electrical signal detected in the imaging area L for each scanning line. For example, an irradiation electrical signal measured in the imaging area L of the light source 21 in advance and likewise digitized according to the irradiated light amount in 256 gradations is subtracted from the image electrical signal for each scanning line and the resulting signal is set as a corrected image electrical signal. This can eliminate an influence when there is nonuniformity in the light amount of the LED 27.

When it is desired to rotationally move the substrate W based on input information in the process of the image processing apparatus 6, a rotation program is output to the motor 9 to rotate the turntable 5. The rotation program is an operation program of, e.g. stopping the rotation after making a certain degree rotation and then stopping the rotation after making a certain degree rotation next. This is stored in the memory of the controller 10 in advance.

Further, the photoelectric converter 4 is connected to the image processing apparatus 6 and the controller 10 for executing an overall control and can automatically detect a state of the EBR line on the substrate W. Specifically, after being amplified and shaped, an output signal of the photoelectric converter 4 is digitized and stored in the memory of the image processing apparatus 6. The information stored in the memory is read by a predetermined means and a predetermined signal processing is performed in the image processing apparatus 6 to judge the presence or absence of a changing point of the EBR line.

When the two-dimensional image of FIG. 6 is obtained, it is divided into the blocks B1, B2 and B3 as shown in FIG. 7 to enhance the edge line L12 (Step S104). Specifically, as described above, the gradation values of the pixel are integrated at the same pixel position for each line and the integrated value largely different from both the integrated value of the region where the resist film is present and that of the region where the resist film is absent is deleted. Since there is a high possibility that such an intermediate integrated value is found in the region where the resist film is absent, the integrated value of that pixel is set equal to that of the region where the resist film is absent. In other words, luminance becomes lower than in the region where the resist film is absent due the presence of the resist film in a part of the region where the resist film is absent. In such a case, it is not judged as the edge line L12 and an error judgment in the extraction of the edge line L12 is prevented by setting the gradation value equal to that of the region where the resist film is absent. Thereafter, the integrated values of each of the blocks B1, B2 and B3 are expanded into a two-dimensional image to reconfigure the two-dimensional image shown in FIG. 6.

By extracting the EBR line as one representing a luminance difference beyond a preset range over the entire periphery based on the image electrical signal at a position distant from the center of rotation A0 of the substrate W for this two-dimensional image subjected to the enhancement process as shown in FIG. 7, the edge line L12 is obtained. At the substantially center of rotation A0 side, i.e. at the inner side of the edge line L12, there is no coating film formation nonuniformity, the amount of the reflected light is small and weak light is obtained. At the outer side of the edge line L12, the amount of the reflected light is large, strong light is obtained, and a gradation difference associated with that appears. Thus, if the two-dimensional image is obtained, a boundary between an area where the gradation value is high and an area where the gradation value is low appears. This boundary is extracted by being compared with a preset gradation difference and the edge line L12 is specified. Note that although this edge line L12 is expressed as indicating the boundary for the sake of convenience, it actually means only a boundary between areas on the left and right sides of the edge line L12 shown in FIG. 7 on the two-dimensional image and a line is not recognized.

As described above, since the irradiated light is scanned in the radial direction of the substrate W, an electrical signal output from the photoelectric converter 4 is linear and signal processing such as computation in the image processing apparatus 6 becomes easier.

Figure 9:
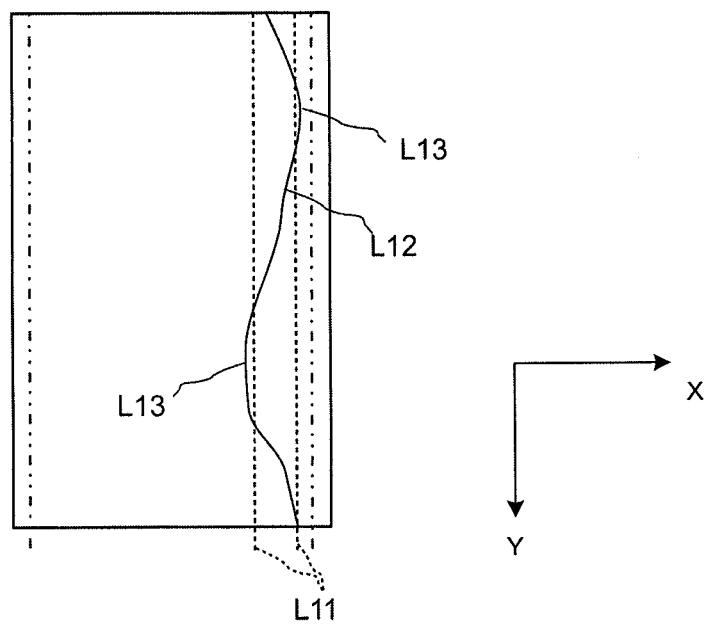
FIG. 9 is a diagram showing a changing point by the EBR line and the judgment band.

Subsequently, the changing point is judged by superimposing the judgment band on the two-dimensional image (Step S105). FIG. 9 is a diagram for explaining a changing point judgment. As shown in FIG. 9, if the edge line L12 largely varies, it includes regions located beyond the width of the judgment band L1 shown by dotted line. These regions are judged as changing points L13 of the edge line L12. Specifically, the evaluator 61 judges the absence of the edge line L12 within the width of the judgment band L11 for each scanning line. In other words, the absence of the boundary between the area where the resist film is present and the area where the resist film is absent within the width of the judgment band L11 is judged. Since the width of the judgment band L11 indicates the coated position of a desired resist film, the controller 10 outputs a signal indicating an edge defect to the display if the absence of the edge line L12 within the width of the judgment band L11 is detected in this judgment result.

Further, the area of the edge part on the substrate W is evaluated by detecting this changing point L13. Specifically, if many changing points L13 are detected, it means that the resist film is not applied in a desired area of the substrate W. In this case, the changing points are extracted on the entire periphery of the substrate W.

The judgment band L11 is set in the evaluator 61 by the following process. A plurality of substrates W to which a resist is applied are empirically measured in advance. As a result, a level for judging a boundary between an application area and an edge area is obtained and set on a signal. An edge defect is easily detecting by comparing this with a concave changing point L13 of the EBR line of the substrate W to be inspected in an actual inspection step. Since the edge line L13 is normally mostly located within the width of the judgment band L11, there is an effect of simplifying the process by setting to judge a case where the edge line L12 is not located within the width of the judgment band L11 here.

Specifically, when the amount of the reflected light is digitized to form the two-dimensional image as described above, the changing point L13 can be detected on the entire periphery of the substrate W. Thus, the inspection can be efficiently performed. Further, in the case of judging an edge defect, it is not necessary to judge the position of the edge line L12 for each line and it is sufficient to detect only the case where the edge line L12 is not located within the width of the judgment band L11, wherefore the process is easily performed.

As just described, by judging the presence or absence of the edge line L12 on the judgment band L11 as shown in FIG. 9 in the controller 10, the case where the edge line L12 is absent within the width is judged to be the presence of the changing point L13. The presence of an edge defect is judged when the edge line L12 is absent within the width of the judgment band L11. In this way, in the substrate inspection apparatus 100 of the above embodiment, the EBR line indicating a change in a relatively large range can be reliably detected by a simple configuration.

Note that although the changing point L13 is judged in the evaluator 61 in the above embodiment, the judgment may be made in the controller 10. Further, the inspection result may be displayed on a television monitor provided in the substrate inspection apparatus 100.

Finally, when whether the edge of the substrate W as an inspection target is good or band is judged, the substrate W is unloaded from the turntable 5, assuming that the inspection process has been finished (Step S106). In this unloading step, it is not necessary to adjust the position of the turntable 5 anew since the orientation of the substrate W is the same as at the time of loading. Specifically, since the inspection is performed by capturing the two-dimensional image of the substrate W during one turn of the substrate W in the inspection process, the inspection process is finished with the substrate W held in the same orientation as at the time of loading. Thus, there is an advantage that the orientation of the substrate W needs not be adjusted anew in unloading the substrate W on the turntable 5 by a conveyor.

As described above, according to the above embodiment, the two-dimensional image of the substrate W is generated and the presence of an edge defect is judged when the edge line L12 is absent within the width of the judgment band L11. In this way, an edge defect can be reliably detected by a simple configuration by judging the EBR line indicating a change in a relative large range in the substrate inspection apparatus 100.

Note that although the edge line L12 is detected as the boundary between the areas on the left and right sides of the edge line L12 shown in FIG. 7 on the two-dimensional image in the above embodiment, this boundary may be recognized as a line. Specifically, after the two-dimensional image is expanded into the two-dimensional image again after the enhancement process, a boundary position corresponding to the edge line L12 may be recognized and judged as a line.

Another effect brought about by performing the enhancement process (Step S104) of the above embodiment is described. If an uneven pattern is formed on the substrate W and the resist film is applied to the upper surface thereof, not only gradation values of an image based on the presence or absence of the resist film, but also shade caused by the pattern of the lower layer are reflected on the captured two-dimensional image. In this case, the gradation values vary particularly in the region where the resist film is present and there would a potential for an error detection depending on the presetting of the gradation difference to extract the EBR line as indicating the luminance difference beyond the preset range. Thus, by applying the enhancement process to such a two-dimensional image, the integrated value appears as a strong peak in a region corresponding to the edge line L12. This can more reliably prevent an error judgment in the extraction of the edge line L12.

Further, although the number of the blocks to which the enhancement process is applied is three in the above embodiment, there is no limitation to this and an appropriate number may be set. In this case, since the effect of the enhancement process is weakened if the number is large and the process takes time if the number is small, the number may be set in consideration of process efficiency.

Further, although the enhancement process is performed in the above embodiment, it is not essential to perform the enhancement process. For example, a residue of the resist film may only slightly affect the integration result. In this case, the integrated value of the pixel corresponding to the residue is substantially the same as that of the high-luminance region (i.e. region where no residue is present) and the judgment process may be immediately performed without performing the enhancement process (Step S104).

Figure 10:
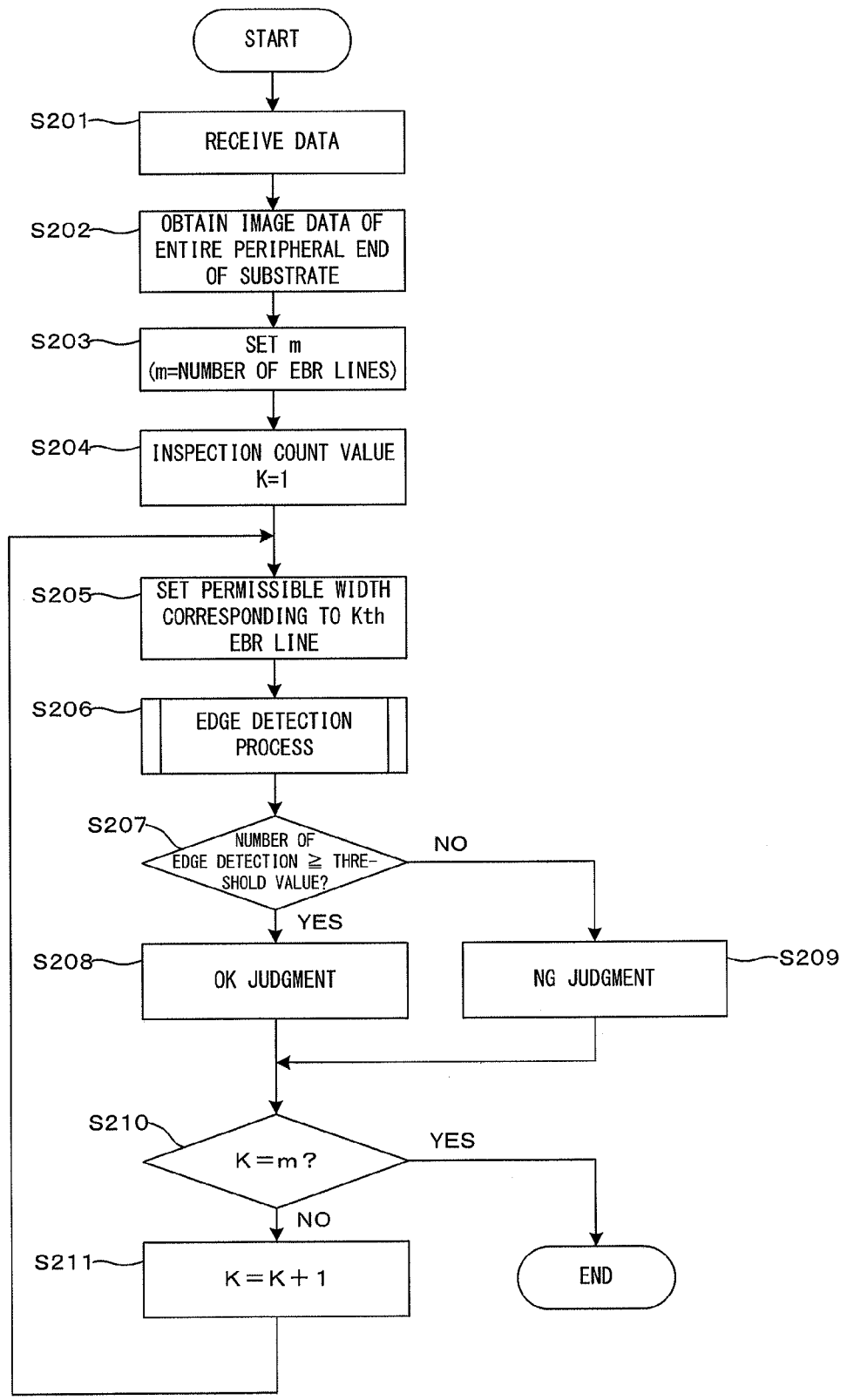
FIG. 10 is a flow chart showing an operation of a second embodiment of the coating film formation nonuniformity inspection apparatus.
Figure 11:
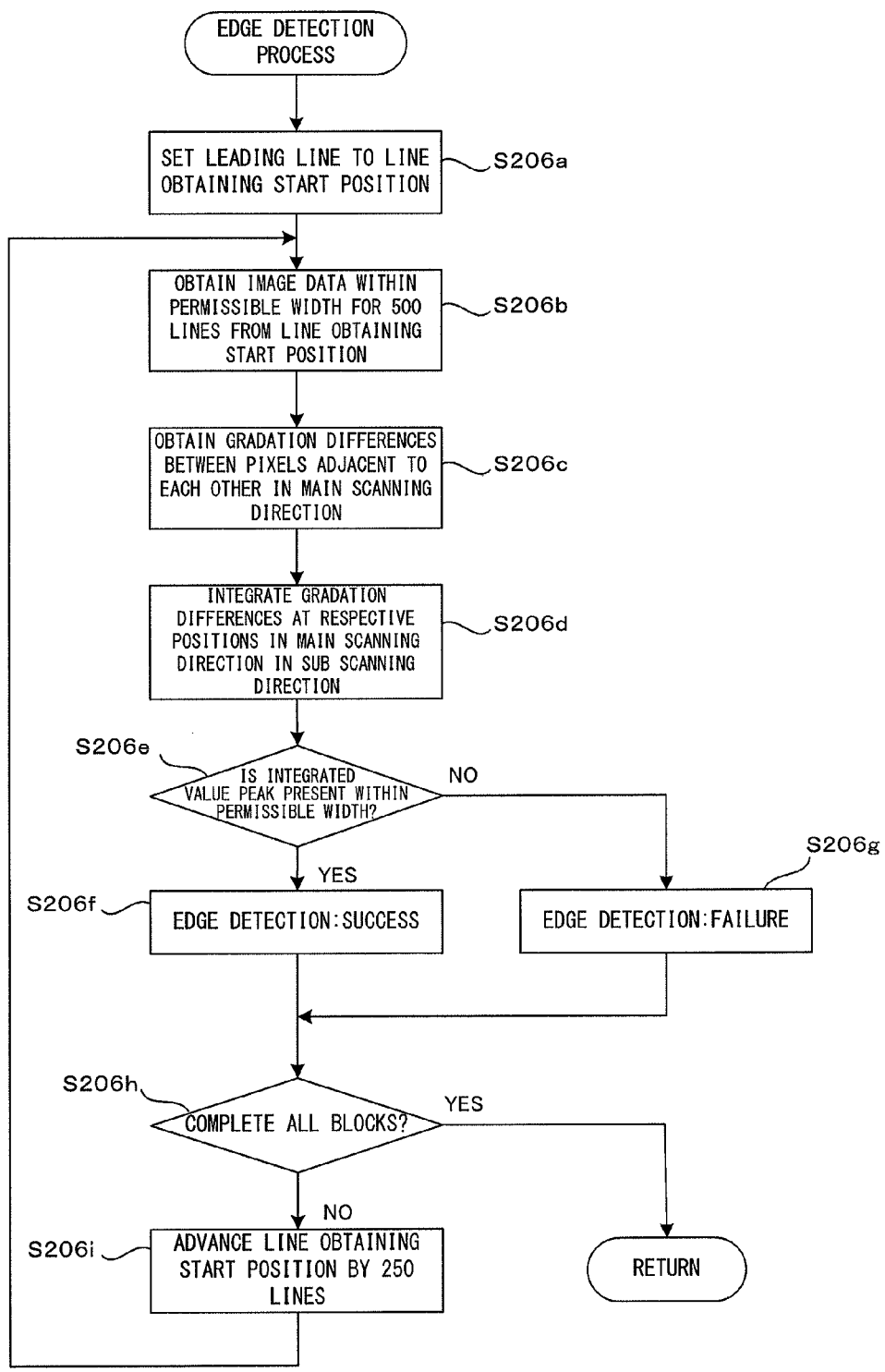
FIG. 11 is a flow chart showing an edge detection operation in the second embodiment.

FIG. 10 is a flow chart showing the operation of a second embodiment of a coating film formation nonuniformity inspection apparatus. Further, FIG. 11 is a flow chart showing an edge detection operation in the second embodiment. This second embodiment is common to the first embodiment in that an edge defect is judged by using a judgment band for a two-dimensional image obtained by the apparatus shown in FIG. 1, but the edge defect is judged by a substrate inspection method different from the enhancement process (Step S104) and the judging process (Step S105) of the first embodiment. Specifically, the processes excluding the enhancement process (S104) and the judging process (Step S105), i.e. the substrate loading process (Step S101), the exposure starting process (Step S102), the imaging process (Step S103) and the substrate unloading process (Step S106) are basically the same as those of the first embodiment, whereas edge detection and edge defect judgment based on the edge detection largely differ from those of the first embodiment. The substrate inspection method in the second embodiment is described, centering on points of difference.

Figure 12B:
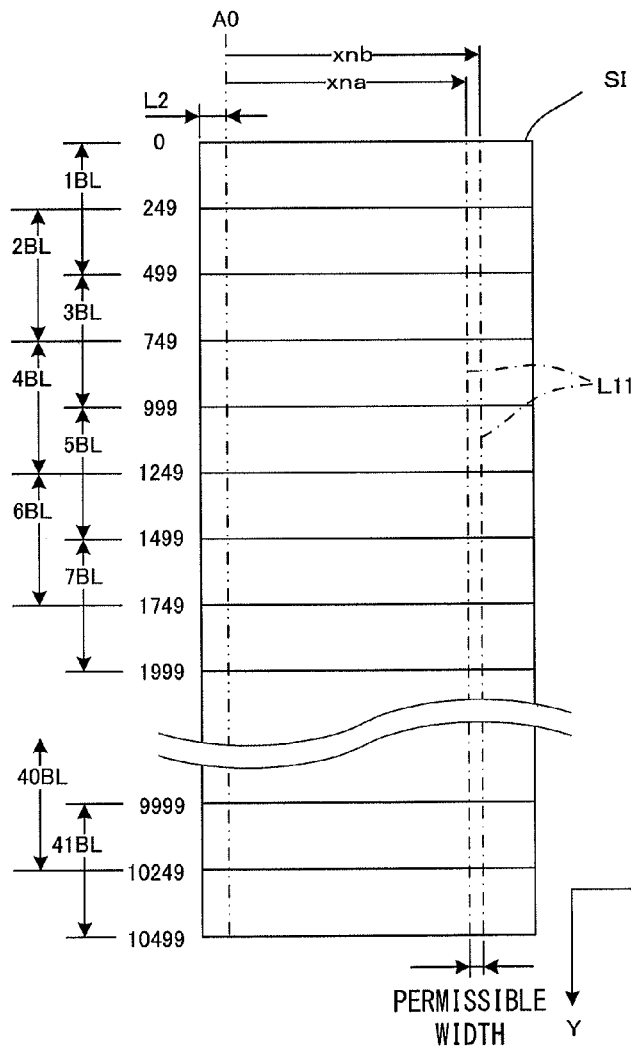
FIG. 12 is a diagram showing a relationship between the EBR line and the judgment band, and a relationship between the judgment band and the edge position.
Figure 12C:
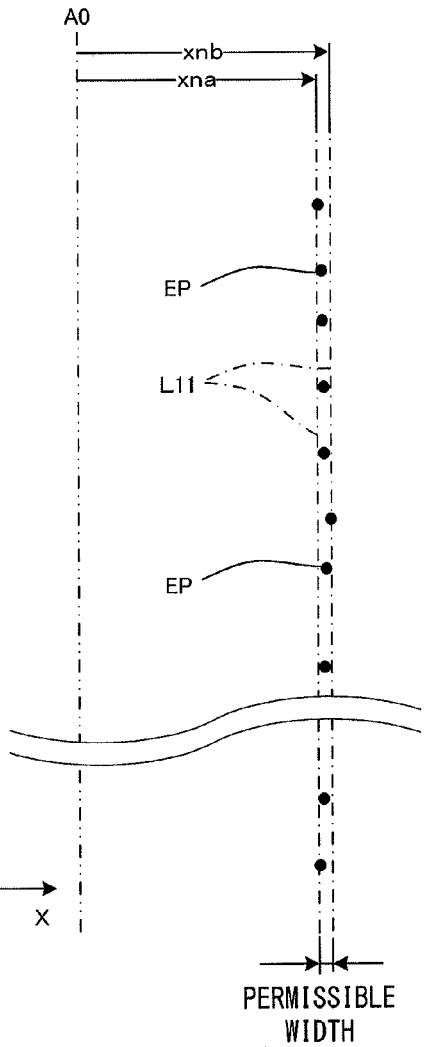

In this second embodiment, the image processing apparatus 6 receives data indicating a relationship between the EBR line and the judgment band and stores it in an unillustrated memory (Step S201) before obtaining a two-dimensional image. The image processing apparatus 6 having received the above data stores permissible widths of the judgment band L11 to detect each EBR line formed on the surface of the substrate W in a table format in the memory by respective processings 1, 2, . . . , n, for example, as shown in FIG. 12A. "Inner diameter xna in FIG. 12A means a distance from the center of rotation A0 to an end of the judgment band L11 facing the center of rotation, "outer diameter xnb" means a distance from the center of rotation A0 to an end of the judgment band L11 opposite to the center of rotation, and the judgment band L11 and the permissible range of the judgment band L11 are specified by these inner diameter and the outer diameter. For example, if m coated films are formed and laminated on the surface of the substrate W by the processing n and m EBR lines are present, the permissible width (xn1a to xn1b), (xn2a to xn2b), (xnma to xnmb) of the judgment band L11 is set for each ERB line. Accordingly, it means a success in edge detection that an edge position EP of the EBR line calculated as described later is located within the permissible width of the judgment band L11 (FIG. 12C) and, conversely, it means a failure in edge detection that the edge position EP is not located within the permissible width. Note that the permissible widths (Xna to xnb) are individually set for the respective processings 1, 2, . . . , n and the respective ERB lines because the number, type and size of the films formed on the surface of the substrate W differ depending on the content of the processing.

When the substrate W as an inspection target is placed on the turntable 5, the image processing apparatus 6 obtains a two-dimensional image Si indicating the entire surface of the substrate W by obtaining 10500 images of a scanning line captured every 360 μsec while the substrate W held on the turntable 5 is making one turn about the center of rotation A0 and arranging the obtained images in the sub scanning direction Y perpendicular to the main scanning direction X (FIG. 12B) as in the first embodiment. Further, in this embodiment, the image processing apparatus 6 extracts a two-dimensional image EI (FIG. 13A) indicating the entire periphery of a peripheral edge part of the substrate W from the two-dimensional image SI of the entire substrate surface and temporarily stores image data of that image EI in the memory (Step S202). Subsequently, the image processing apparatus 6 performs the following processes based on the image data of the image EI (Steps S203 to S211).

In Step S203, the number m of the EBR lines corresponding to the processing applied to the substrate W held on the turntable 5 is read from the data received in Step S201 and set. Further, an inspection count value K is set to an initial value "1" (Step S204). This inspection count value K is a value indicating the order of the EBR line being inspected and the EBR line as an inspection target is specified by this inspection count value K.

In subsequent Step S205, the permissible width (xna to xnb) of the judgment band L11 corresponding to the EBR line indicated by the inspection count value, i.e. the $K^{th}$ EBR line is read from the table (FIG. 12A) in the memory and set. Then, an edge detection process is performed using that judgment band L11 and the edge of the $K^{th}$ EBR line is detected from the image data (Step S206).

The summary of the operation of this edge detection process is as follows. That is, as shown in FIGS. 13, a block image BI located within the permissible width (Xna to Xnb) of the judgment band L11 and corresponding to 500 lines in the sub scanning direction Y is extracted, and whether or not the edge of the EBR line is included in the block image BI is judged based on block image data BD of this block image BI. In this embodiment, the edge detection is performed for a total of 41 block images BI while the block image BI is shifted by 250 lines in the sub scanning direction Y every time.

Next, the edge detection process is described in detail with reference to FIGS. 11 to 13. The image processing apparatus 6 performs the edge detection process in accordance with an operation flow shown in FIG. 11. In this edge detection process, the leading line of the block image BI is first set to the $0^{th}$ line which is an initial value of a line obtaining start position (Step S206a). Then, the image data within the permissible width (Xna to Xnb) of the judgment band L11 set in Step S205 is obtained out of the image data of the two-dimensional image EI of the entire peripheral end of the substrate for 500 lines from the line obtaining start position to extract the block image BI (Step S206b). Then, gradation differences ΔD between image data of pixels adjacent to each other in the main scanning direction X out of pixels constituting the block image BI are calculated and gradation difference data DD including these is stored in the memory (Step S206c). For example, in FIGS. 13B and 13C, a gradation difference ΔD (Xna+p, 0) of adjacent pixels (Xna+p, 0), (Xna+p+1, 0) is calculated by:

$$\Delta D(Xna+p, 0) = D(Xna+p+1, 0) - D(Xna+P, 0)$$

where p is a natural number not smaller than 0 and not larger than (Xnb−Xna−1).

Then, the gradation differences ΔD at the respective positions (Xna to Xnb) in the main scanning direction X are integrated in the sub scanning direction Y (Step S206d). Here, if the edge of the EBR line is included in the block image BI, the gradation differences ΔD at the edge positions EP are relatively large, whereas the gradation differences ΔD indicate zero or a value approximate to zero at non-edge positions. In addition, since the gradation differences ΔD at the respective positions (Xna to Xnb) are integrated, the influence of noise and the like can be suppressed. For example, as shown in FIG. 13D, the integrated value at the edge position is considerably higher than at the non-edge positions. Accordingly, in this embodiment, whether or not an integrated value peak exceeding 2σ (σ: standard deviation) from an average value of the integrated values out of the integrated values within the permissible width (Xna to Xnb) of the judgment band L11 is judged (Step S206e). For example, if this peak is present at a position (Xna+p) as shown in FIG. 13D ("YES" in Step S206e), a success in edge detection is judged (Step S206f). On the other hand, if no integrated value peak is confirmed ("NO" in Step S206e), a failure in edge detection is judged (Step S206g).

When a judgment as to whether or not the edge of the EBR line is included in this block image BI is completed in this way, a return is made to Step S206b and a series of processings (Step S206b to S206h) described above are performed for the next block image BI after the line obtaining start position is advanced by 250 lines in the sub scanning direction Y (Step S206i) while a judgment on the presence or absence of the edge is not completed for a total of 41 block images (while "NO" in Step S206h). When the judgment on the presence or absence of the edge is completed for a total of 41 block images, a total of 41 judgment results are obtained. Thus, a transition is made to Step S207 by closing the edge detection process.

Referring back to FIG. 10, the operation is further described. In this Step S207, whether or not the number of the judgment results indicating the edge detection out of 41 judgment results is not smaller than a preset threshold value, e.g. ¾ of 41 is judged. If this number is not smaller than the threshold value, it is judged that the edge line is located in the judgment band L11 and the edge is good (Step S208). On the other hand, if this number is below the threshold value, it is judged that the edge line is not located in the judgment band L11 and the edge is defective (Step S209). Note that a judgment criterion is not limited to the above criterion (the edge was detected in not less than ¾ of the blocks) and may be, for example, empirically obtained.

When the good or bad judgment on the edge for the K$^{th}$ EBR line is completed in this way, whether or not the inspection count value K coincides with the number m of the EBR lines is judged (Step S210). If they are at variance, a return is made to Step S205 and a good or bad judgment on the edge is made for the next EBR line after the inspection count value K is incremented by "1". On the other hand, if "YES" in judged in Step S210 and the good or bad judgment on the edge is confirmed to have been completed for all the EBR lines, a series of processes are finished.

As described above, according to the second embodiment of the invention, the evaluation of the coating film can be easily judged from the captured two-dimensional image of the substrate W and inspection/detection with high process efficiency can be made as in the first embodiment. Further, in the second embodiment, whether the EBR line is good or bad can be inspected without obtaining the edge line itself unlike the first embodiment, and the evaluation of the coating film can be more simplified.

Further, a division mode of the block images BI (block line number, block shift unit number in the sub scanning direction Y) is arbitrary. For example, a block image BI composed of 500 lines may be shifted by 500 lines in the sub scanning direction Y. However, by division into the block images BI such that the block images BI adjacent to each other partly overlap in the sub scanning direction as in the second embodiment, the edge positions EP of the EBR lines can be detected with high accuracy and an edge defect can be more precisely judged.

As just described, in the second embodiment, the image processing apparatus 6 functions as an edge detector for detecting the edge positions of the EBR lines in each block image BI and a good or bad judgment unit for judging whether the EBR line is good or bad based on the number of the edge-detected block images BI, but the controller 10 may partly or entirely function as these. That is, as in the first embodiment, the "image processor" of the invention may be composed of the image processing apparatus 6 and a part of the controller 10.

Further, since the permissible width of the judgment band L11 corresponding to each EBR line is preset and the judgment band L11 having the permissible width corresponding to each EBR line is used in the above second embodiment, the good or bad judgment on the edge of each coating film can be highly accurately made also for a substrate on which a plurality of types of coating films are formed. Note that a technical concept of preparing the judgment bands corresponding to the respective coating films in advance and using the judgment band corresponding to each EBR line can also be applied to the first embodiment.

Note that the invention is not limited to the above embodiments and various changes other than those described above can be made without departing from the gist of the invention. For example, although the image processing apparatus 6 and the controller 10 are separate structures in the above embodiments, they may be configured as an integral processor having similar control functions.

Further, although the coating target is a circular substrate in the above embodiments, rectangular substrates such as glass substrates and color filters having a planar quadrilateral shape, a planar trapezoidal shape or the like may be coating targets if they are targets to be coated while being placed and rotated on a turntable.

INDUSTRIAL APPLICABILITY

A substrate inspection apparatus of the invention can be used to inspect a state of a substrate coated with a film.

REFERENCE SIGNS LIST

1: detection unit
100: substrate inspection apparatus
2: light irradiator
21: light source
3: optical system
4: photoelectric converter
5: turntable
6: image processing apparatus
61: evaluator
10: controller
A0: center of rotation (of a substrate)
BI: block image
L: imaging area
L11: judgment band
L12: edge line
W: substrate

The invention claimed is:
1. A substrate inspection apparatus, comprising:
a rotator that holds and rotates a substrate having a coating film formed on a surface;
a light irradiator that irradiates light to the surface of the substrate;

photoelectric converter that receives specularly reflected light from the surface of the substrate and captures an image of a scanning line having at least a length of the radius of the substrate in a main scanning direction parallel to a radial direction of the substrate from a center of rotation of the substrate; and an image processor that generates a two-dimensional image by arranging images captured by the photoelectric converter during one turn of the substrate in a sub scanning direction perpendicular to the main scanning direction and judges whether an edge line of the coating film is good or bad using a judgment band set in parallel to the sub scanning direction for the two-dimensional image, wherein the image processor includes:

an edge detector that divides an image included in the judgment band out of the two-dimensional image into a plurality of block images in the sub scanning direction and detects whether or not each block image includes the edge of the coating film; and a good and bad judgment unit that judges whether the edge line of the coating film is good or bad based on the number of the edge-detected block images by the edge detector.

2. The substrate inspection apparatus according to claim 1, wherein the edge detector divides the image such that the block images adjacent to each other partly overlap in the sub scanning direction.

3. The substrate inspection apparatus according to claim 1, wherein the image processor specifies the edge line included in the two-dimensional image, calculates a changing point based on the presence or absence of the edge line within the width of the judgment band and judges an edge defect in the absence of the edge line.

4. The substrate inspection apparatus according to claim 1, wherein:

a plurality of coating films are laminated on the surface of the substrate;

judgment bands are set in correspondence with the respective coating films; and the image processor judges whether an edge line of each coating film is good or bad using the judgment band corresponding to each coating film.

5. A substrate inspection apparatus, comprising:

a rotator that holds and rotates a substrate having a coating film formed on a surface;

a light irradiator that irradiates light to the surface of the substrate;

a photoelectric converter that receives specularly reflected light from the surface of the substrate and captures an image of a scanning line having at least a length of the radius of the substrate in a main scanning direction parallel to a radial direction of the substrate from a center of rotation of the substrate; and an image processor that generates a two-dimensional image by arranging images captured by the photoelectric converter during one turn of the substrate in a sub scanning direction perpendicular to the main scanning direction and judges whether an edge line of the coating film is good or bad using a judgment band set in parallel to the sub scanning direction for the two-dimensional image, wherein the scanning line captured by the photoelectric converter has a length which is the sum of the radius of the substrate and a first length in the main scanning direction from the center of rotation.

6. The substrate inspection apparatus according to claim 5, wherein the scanning line captured by the photoelectric converter extends a second length in a direction opposite to the main scanning direction from the center of rotation.

7. A substrate inspection apparatus, comprising:

a rotator that holds and rotates a substrate having a coating film formed on a surface;

a light irradiator that irradiates light to the surface of the substrate;

a photoelectric converter that receives specularly reflected light from the surface of the substrate and captures an image of a scanning line having at least a length of the radius of the substrate in a main scanning direction parallel to a radial direction of the substrate from a center of rotation of the substrate; and an image processor that generates a two-dimensional image by arranging images captured by the photoelectric converter during one turn of the substrate in a sub scanning direction perpendicular to the main scanning direction and judges whether an edge line of the coating film is good or bad using a judgment band set in parallel to the sub scanning direction for the two-dimensional image, wherein the scanning line captured by the photoelectric converter extends a length in a direction opposite to the main scanning direction from the center of rotation.

8. A substrate inspection method, comprising:

a capturing step of capturing an image of a scanning line having at least a length of the radius of a substrate having a coating film formed on the surface in a main scanning direction parallel to a radial direction of the substrate from a center of rotation of the substrate by irradiating light to the surface of the substrate while rotating the substrate, and receiving specularly reflected light from the surface of the substrate;

an image generating step of generating a two-dimensional image by arranging images obtained by repeating the capturing step during one turn of the substrate in a sub scanning direction perpendicular to the main scanning direction; and a judging step of judging whether an edge line of the coating film is good or bad using a judgment band set in parallel to the sub scanning direction for the two-dimensional image, wherein the judging step includes: dividing an image included in the judgment band out of the two-dimensional image into a plurality of block images in the sub scanning direction and detecting whether or not each block image includes the edge of the coating film, and judging whether the edge line of the coating film is good or bad based on the number of the edge-detected block images.

9. The substrate inspection method according to claim 8, wherein the judging step includes dividing the image such that the block images adjacent to each other partly overlap in the sub scanning direction.

10. The substrate inspection method according to claim 8, wherein the image generating step includes specifying the edge line included in the two-dimensional image, calculating a changing point based on the presence or absence of the edge line within the width of the judgment band, and judging an edge defect in the absence of the edge line.

11. The substrate inspection method according to claim 8, wherein the scanning line captured in the capturing step has a length which is the sum of the radius of the substrate and a first length in the main scanning direction from the center of rotation.

12. The substrate inspection method according to claim 11, wherein the scanning line captured in the capturing step extends a second length in a direction opposite to the main scanning direction from the center of rotation.

13. The substrate inspection method according to claim 8, wherein the scanning line captured in the capturing step extends a length in a direction opposite to the main scanning direction from the center of rotation.

14. The substrate inspection method according to claim 8, wherein:
- a plurality of coating films are laminated on the surface of the substrate; and
- in the judging step, a plurality of judgment bands are set in correspondence with the respective coating films; and
- the step of judging whether an edge line of each coating film is good or bad uses the respective judgment band corresponding to each coating film.

* * * * *